Figure 1:
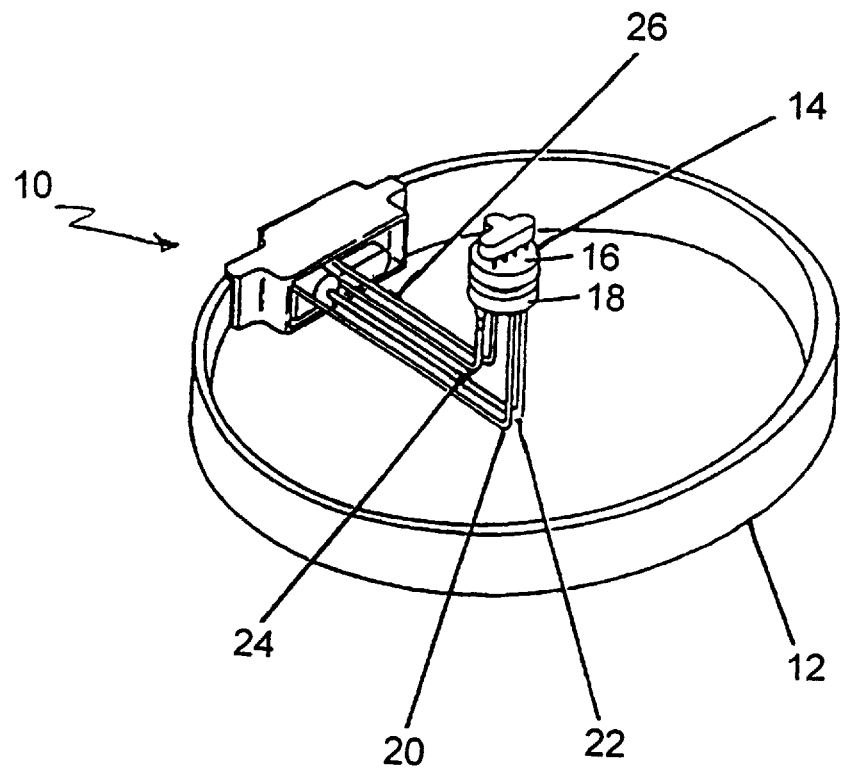
Figure 2:
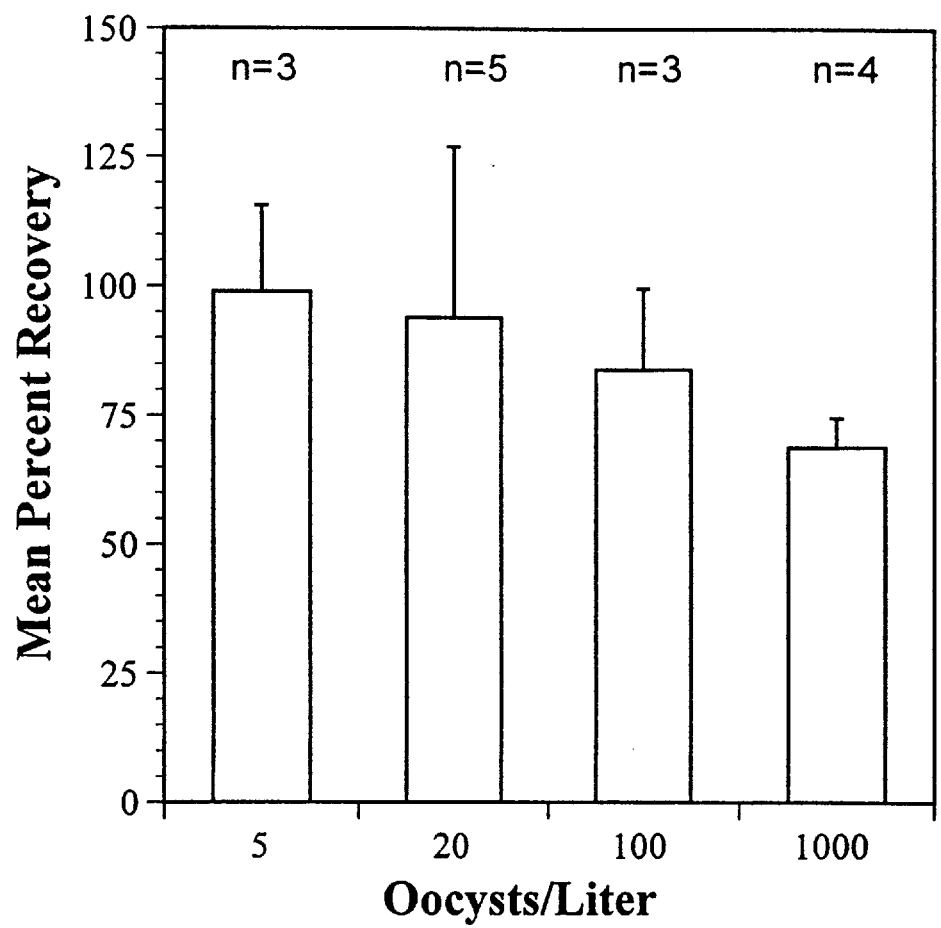
Figure 3:
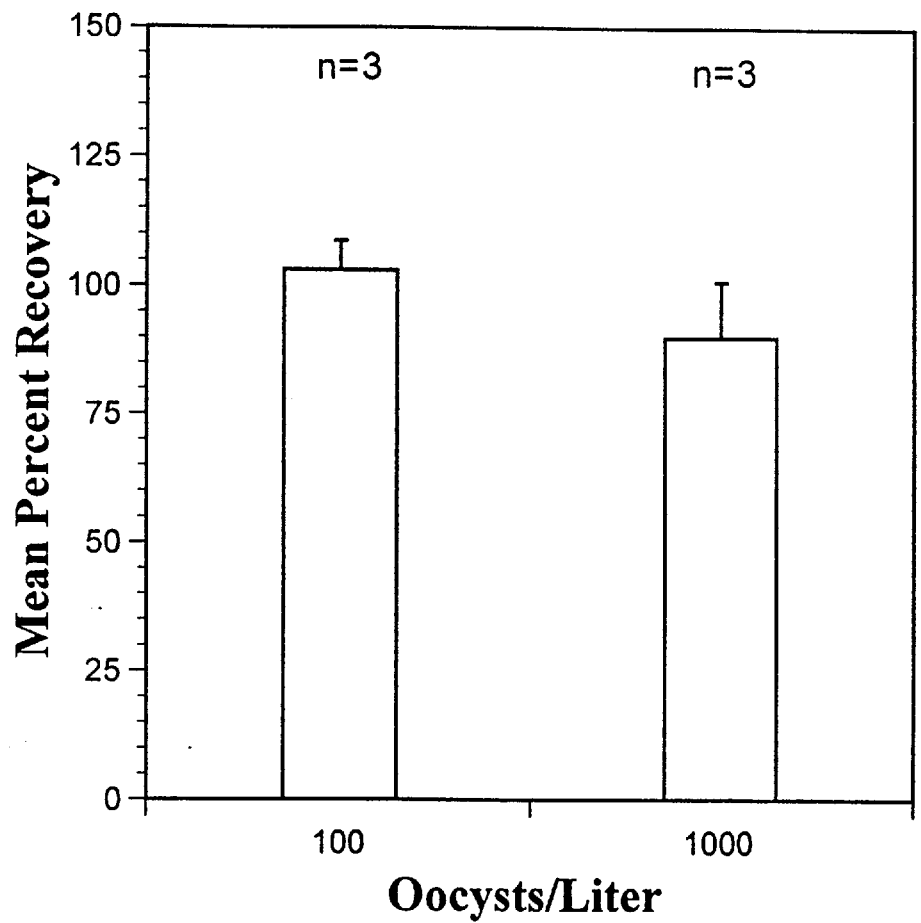

United States Patent [19]
Borchardt et al.

[11] Patent Number: 5,846,439
[45] Date of Patent: Dec. 8, 1998

[54] METHOD OF CONCENTRATING WATERBORNE PROTOZOAN PARASITES

[75] Inventors: Mark A. Borchardt, Marshfield; Susan Spencer, Spencer, both of Wis.

[73] Assignee: Marshfield Medical Research & Education Foundation, a Division of Marshfield Clinic, Marshfield, Wis.

[21] Appl. No.: 608,422

[22] Filed: Feb. 28, 1996

[51] Int. Cl.$^6$ ........................................ B01P 21/26
[52] U.S. Cl. .................... 210/781; 210/787; 422/72; 494/43
[58] Field of Search ............... 210/360.1, 380.1, 210/435, 781, 787; 422/72, 101; 494/41, 43, 70; 209/173

[56] References Cited

U.S. PATENT DOCUMENTS

| | | | |
|---|---|---|---|
| 3,217,982 | 11/1965 | Wilsmann et al. | 494/70 |
| 4,010,894 | 3/1977 | Kellogg et al. | 494/45 |
| 4,419,089 | 12/1983 | Kolobow et al. | 494/45 |
| 4,816,149 | 3/1989 | Wekell | 210/435 |

*Primary Examiner*—David A. Reifsnyder
*Attorney, Agent, or Firm*—DeWitt Ross & Stevens S.C.

[57] ABSTRACT

A method of concentrating oocysts of waterborne protozoan parasites from water potentially contaminated by dilute densities of the parasites is described. Potentially contaminated water is fed into the separation channel of a continuous separation channel centrifuge. The water is centrifuged for a period of time sufficient to collect the parasitic oocysts and cysts in the channel.

10 Claims, 7 Drawing Sheets

METHOD OF CONCENTRATING WATERBORNE PROTOZOAN PARASITES

FIELD OF THE INVENTION

The present invention is directed in general to a method of concentrating waterborne protozoan parasites from water potentially contaminated by dilute densities of the parasites. More particularly, the present invention is directed to a method of concentrating dilute densities of the pathogenic *Cryptosporidium spp.* and *Giardia spp.* from potentially contaminated water.

BACKGROUND OF THE INVENTION

Severe outbreaks of gastroenteritis have been caused by the environmentally resistant intestinal protozoan parasites *Cryptosporidium* and *Giardia lamblia*. These organisms are often waterborne, existing in very dilute densities in public water supplies.

The protozoan parasite Cryptosporidium has been linked to waterborne outbreaks of gastroenteritis since 1987, when 13,000 residents of Carrolton, Ga. contracted waterborne cryptosporidiosis. The oocysts can survive for long times in water and are resistant to routine water treatment methods such as chlorination or ozonation. The presence in source waters of even small numbers of Cryptosporidium oocysts is a matter of concern, because the infective dose for humans is possibly as low as one oocyst.

Clearly, the detection of both parasites in water supplies is a critical societal problem. The central issue in detection of the parasites is how to concentrate dilute densities of the protozoa from large volumes of water so as to detect the presence of Cryptosporidium and Giardia. The method currently recommended by the Environmental Protection Agency (EPA) and the American Society for Testing and Materials (ASTM) concentrates the protozoa by sampling 100 liters (or more) of water through a polypropylene yarn cartridge filter.

As summarized in Nieminski et al., *Applied and Environmental Microbiology*, 61(5): 1714–1719, 1995, in the ASTM method, after sampling, particulates from the cartridge filter are extracted by cutting the filter apart and washing the fibers. The extracted particulates are then concentrated by centrifugation. The concentrated particulates are then processed to selectively concentrate cysts and oocysts by floatation in 50-ml tubes on a Percoll-sucrose gradient. Particulates recovered at the interface of the Percollsucrose gradient are stained with fluorescently tagged antibodies on 25-mm-diameter, $0.2\mu$ m-pore-size cellulose acetate filters. After mounting on slides, the membrane filters are scanned with an epifluorescent microscope for objects of the right size, shape and fluorescence characteristic of Cryptosporidium oocysts and Giardia cysts. On finding such objects, the microscope optics are switched to phase contrast to look for internal morphological characteristics inside the detected organisms. Organisms determined to meet the fluorescence detection criteria are counted as presumptive Cryptosporidium oocysts. Organisms with the right fluorescence characteristics and shown to have the respective internal morphological characteristics are counted as confirmed Cryptosporidium oocysts.

However, the ASTM method is costly and time consuming. Furthermore, losses of oocysts occur throughout the procedure. Large numbers pass through the filter, or adhere to the filter material and are not recovered. Losses also occur during centrifugation because oocysts are destroyed or resuspended during removal of the supernatant fluid. During a recent blind test of commercial laboratories in the United States, spiked samples were submitted to 16 laboratories to evaluate their ability to recover and detect Cryptosporidium using the ASTM method. Six failed to recover any Cryptosporidium oocysts, and 10 had an average recovery rate of only 2.8%. Aldom, et al., *Letters in Applied Microbiology* 20: 186–187, 1995. A more detailed description of losses of Cryptosporidium oocysts during the detection procedure can be found in LeChevallier et al., *Applied and Environmental Microbiology* 61 (2): 690–697, 1995.

Several studies have been conducted on techniques to improve the efficiencies of methods for concentrating the dilute protozoa. The general protocol in such tests is to spike a water sample with a known amount of Cryptosporidium oocysts, and determine the percentage of oocysts recovered for each method tested.

For example, other types of filtration have been evaluated, including vortex-flow, cross-flow or tangential, and sand column. Whitmore et al., *Wat. Sci. Tech.* 27 (3-4): 69–76, 1993. In the Whitmore et al. study, the vortex-flow filtration technique gave fairly consistent recoveries of 30% to 40%. However, the comparatively long process times would prevent the use of this method for monitoring purposes. The cross-flow or tangential filtration module gave relatively good recoveries (approximately 40–80%) at moderately high flow rates. The laboratory scale sand columns evaluated gave satisfactory retention within the column material at low flow rates. However, the sand column system was judged inadequate for monitoring because of the poor retention of oocysts within the column matrix at realistic flow rates. Another study tested a filter matrix dissolution method to recover Cryptosporidium oocysts from water. The average recovery rate observed was 70.5%. Aldom, et al., *Letters in Applied Microbiology* 20: 186–187, 1995. Cryptosporidium oocysts have also been concentrated from water by "sweeping" water with a settling calcium carbonate precipitate. Vesey et al., *Journal of Applied Bacteriology* 75: 82–86, 1993. The Vesey et al. study resulted in a 68% recovery of oocysts from seeded samples of deionized, tap and river water.

Continuous centrifugation has also been studied as a means to concentrate the dilute Cryptosporidium oocysts. There are two types of continuous centrifuges, bowl centrifuges and channel centrifuges. So far, only two studies have examined continuous centrifugation as a method for concentrating Cryptosporidium, and both studies used a bowl-type centrifuge. The Whitmore et al. studies cited above evaluated a bowl-type continuous flow centrifuge, with observed recovery of oocysts between 11 to 31.2%. Goatcher et al. also tested a bowl-type continuous flow centrifuge system to collect water samples to minimize loss of the protozoa prior to purification and detection. The study reported recovery rates of between 2 to 20 times that observed with conventional filtration; such a recovery rate therefore, is still well under 50%. Goatcher et al., *American Society of Macrobiology Abstracts* Q-212, 1995.

Thus, it is clearly desirable to develop a method to concentrate Cryptosporidium oocysts and Giardia cysts in order that the presence of these dangerous parasites can be more reliably detected.

SUMMARY OF THE INVENTION

In one embodiment, this invention provides a method of concentrating waterborne protozoan parasites from water potentially contaminated by dilute densities of the parasites. The water is fed to the separation channel of a continuous separation channel centrifuge. The water is centrifuged for a period of time sufficient to collect the parasitic oocysts and cysts in the channel.

It is an object of the present invention to provide a method of concentrating dilute densities of waterborne protozoan parasites from water potentially contaminated with the parasites.

It is another object of the present invention to provide a method of concentrating Cryptosporidium and Giardia from water contaminated with dilute densities of the parasites.

It is another object of the present invention to provide a less costly and time consuming method of detecting Cryptosporidium and Giardia in water.

It is another object of the present invention to provide a continuous method of concentrating Cryptosporidium and Giardia in water.

Other features and advantages of the invention will be apparent from the following description of the preferred embodiments thereof and from the claims.

BRIEF DESCRIPTION OF THE DRAWINGS

FIG. 1 is a diagram of a separation channel of a continuous centrifuge.

FIG. 2 is a graph presenting results of recovery of Cryptosporidium oocysts from phosphate buffered saline.

FIG. 3 is a graph presenting results of recovery of Cryptosporidium oocysts from pond water.

FIG. 4 is a graph presenting results of recovery of Cryptosporidium oocysts as a function of centrifuge flow rate.

FIG. 5 is a graph presenting results of recovery of Cryptosporidium oocysts from pond water with a centrifuge flow rate of 150 mL/min.

FIG. 6 is a graph presenting results of recovery of *Giardia lamblia* cysts from pond water.

FIG. 7 is a graphical representation of the results of the experiments of Example 7 below.

DETAILED DESCRIPTION OF THE INVENTION

The present invention describes a method of concentrating dilute densities of waterborne protozoan parasites from water potentially contaminated by the parasites. Examples of such parasites include *Cryptosporidium ssp.* and *Giardia spp.*, especially *G. lamblia*. While the specification focuses mainly on a description of concentrating dilute densities of Cryptosporidium, the method of the present invention achieves satisfactory results when used to concentrate dilute densities of Giardia as well.

According to the method of the present invention, water which is potentially contaminated with protozoan parasites is pumped into the channel of a continuous flow separation channel centrifuge. The water is centrifuged for a period of time sufficient to collect the parasitic oocysts and cysts in the channel. After centrifugation is complete, the material from the separation channel of the centrifuge is examined for the presence of the parasite by commonly used fluorescent detection methods such as the Merifluour Cryptosporidium/Giardia detection kit, an immunofluorescent assay produced by Meridian Diagnostics, Cincinnati, Ohio.

A separation channel from a typical continuous flow separation channel type of centrifuge, used to concentrate protozoan parasites according to the present invention, is presented in FIG. 1 at reference numeral 10. The separation channel depicted in FIG. 1 is part of a centrifuge manufactured by IBM, model 2997, for use as a blood separator. The division of IBM which manufactured the centrifuge pictured in FIG. 1 is now owned by COBE Corporation, Lakewood, Colo.

When the separation channel unit 10 of FIG. 1 is used as blood separator, blood from a donor's arm is pumped into separation channel 12 as the channel rotates. The various blood components separate, according to their specific gravity, when the blood moves around channel 12 from input to output ports (not shown). To collect the various layers of blood, the output ports are positioned at different fixed distances from the inner walls of channel 12. Plasma and sometimes white cells are collected, while the red cells are returned to the donor via the other arm. The blood separation process occurs continuously.

The unique design feature of the separation channel assembly 10 is rotating seal assembly 14. It consists of two halves: top half 16 is stationary, while bottom half 18 rotates with separation channel 12. The surfaces where the two halves 16 and 18 meet have four concentric matching grooves (not shown) that correspond to whole blood input line 20 and the three output lines 22, 24, and 26, respectively used for plasma, white blood cells, and packed red cells. Whole blood and blood components are transferred from stationary to moving parts through the four grooves. When a centrifuge using the separation channel assembly 10 is used as a blood separator, the input and output lines contain donor safety sensors (not shown) to test for air emboli and pressure irregularities in the tubing.

The hydrodynamic design of the grooves and the viscosity of blood prevent the liquid from leaking between the junction of the two halves 16 and 18 of seal assembly 14, which is open to the atmosphere. Because bloodborne pathogens could potentially leak from the seal and consequently diminish the shelf life of blood products, blood cell separators using a rotating seal assembly have become obsolete.

To concentrate Cryptosporidium from water, the blood cell separator illustrated in FIG. 1 is operated as a simple continuous centrifuge. Water potentially contaminated by dilute densities of Cryptosporidium oocysts is fed into separation channel 12 via whole blood input line 20, at a flow rate in the range of between about 70 mL/min to 500 mL/min, preferably about 150 mL/min. The water is centrifuged at a speed such that the relative gravitational force inside the channel is about 900×g, for a period of time sufficient to collect Cryptosporidium oocysts and *Giardia lamblia* cysts in the channel.

After centrifugation, Cryptosporidium, together with other organisms such as *Giardia lamblia*, inorganic sediment, and detritus, are retained in separation channel 12 rather than being pumped out as usual for blood cells. The supernatant is pumped out via plasma output line 22. The sensors normally present for donor safety are bypassed; unnecessary pumps and circuits are disabled.

In the preferred embodiment of the present invention, water containing 50% glycerin was pumped into the saline port (not shown) of rotating seal assembly 14 using a lubricant pump (not shown) operating at a speed of about 2.5 rpm. The glycerin creates a viscous barrier between water and air at the junction of the two halves 16 and 18 of seal assembly 14 to prevent leaking. Glycerin is not used when centrifuge 10 is used as a blood separator because blood is normally sufficiently viscous to move between stationary and moving halves 16 and 18 without leaking.

Separation channel 12 and associated tubing were primed with water containing a surfactant (for example, preferably 0.001% Tween 80 or Tween 20, obtained from Sigma Chemical Co., St. Louis, Mo.). Coating separation channel 12 with surfactant enhances removal of the collected material containing the parasites after centrifugation is completed; obviously, surfactants are not used when centrifuge 10 is used as a blood separator. Priming was conducted with an output pump (not shown), either the plasma pump built into the centrifuge or a separate additional peristaltic pump (as discussed below).

The centrifuge rotor was then turned on and set at maximum speed, about 2400 rpm, which provides a relative gravitational force inside the rotating channel of approximately 900×g. The output pump was turned on again and the flow rate through separation channel 12 set.

Initial experiments to test the feasibility of centrifuge 10 for concentrating and collecting Cryptosporidium oocysts were conducted at the maximum sample feed rate of the built-in plasma pump, about 70 mL/min. Later experiments used a separate peristaltic pump, not part of centrifuge 10, which was capable of providing a maximum sample feed rate or flow rate of 500 mL/min. Centrifugation took a few minutes to hours depending on the water sample volume. The processing time is normally calculated as the sample volume divided by the sample feed rate. Thus, in general, the centrifugation time necessary to concentrate protozoan samples from typical water samples will be on the order of about ½ to 4 hours, and for smaller samples, times of 1 to 5 minutes of centrifugation have been found sufficient.

After centrifugation was complete, the tubing from seal assembly 14 to separation channel 12 was carefully clamped, the channel removed from the rotor, and the contents drained into a beaker. Channel 12 was then cut in half, filled with 0.01% Tween 80, and the cut ends clamped with Vise Grips. Channel 12 was then shaken vigorously and placed on a laboratory vortex to dislodge any Cryptosporidium that may have adhered to the inner channel walls. This rinsing procedure was conducted several times. The concentrate and all rinses were combined. For these feasibility studies, no further steps were taken to separate Cryptosporidium from debris in the water. Cryptosporidium oocysts were enumerated using standard immunofluorescent procedures.

The invention is further described and illustrated with reference to the following Examples. In all Examples (except for Examples 6, 7, and 8, which used a different type of continuous separation channel centrifuge), the same basic approach was used. An aqueous medium was spiked with a microorganism, usually Cryptosporidium, at a known concentration. The medium was then centrifuged with the centrifuge described in FIG. 1. The material retained in the separation channel was examined for Cryptosporidium oocysts and/or Giardia cysts. Cryptosporidium oocysts and Giardia cysts were detected with the Merifluour Cryptosporidium/Giardia Detection Kit, an immunofluorescent assay produced by Meridian Diagnostics, Cincinnati, Ohio. All results are reported as percent recovery, i.e. total number of organism added to the medium divided by the number recovered in the centrifuge, multiplied by 100.

EXAMPLE 1

Recovery of Cryptosporidium Oocysts from Phosphate-Buffered Saline Solution

Phosphate-buffered saline (PBS) is a simpler aqueous medium than naturally occurring surface or ground water, and, therefore, presumably, would present optimum conditions for concentrating Cryptosporidium oocysts by a continuous separation channel centrifuge. In addition, the experiment tested whether recovery efficiency varied with oocyst concentration, an important consideration given the range of oocyst densities that exist in the environment.

Cryptosporidium oocysts from the positive control of the Merifluour Cryptosporidium/Giardia Detection Kit (Meridian Diagnostics, Cincinnati, Ohio) were diluted with 10% formalin to make a working stock solution having a concentration of approximately 5000 oocysts/mL.

Oocysts were spiked into 2 or 5 L of PBS to achieve the following four target concentrations: 1000, 100, 20 or 5 oocysts/L. Oocysts were recovered using as a continuous separation channel centrifuge the IBM 2997 blood cell separator described above. The centrifuge feed rate was set at 70 mL/min, and the rotor speed was 2200 rpm (relative centrifugal force of 740×g). The total centrifuge time was ½ to 1 hour per sample. The recovery efficiency of the centrifuge was tested 3 to 5 times at each oocyst concentration.

The material from the separation chamber was tested for oocyst presence. The supernatant was also collected, concentrated by bulk centrifugation at 10000×g for 15 min, and the pellets were analyzed for oocysts in the same manner. The results, presented in FIG. 2, show that Cryptosporidium recoveries of greater than 69% were achieved, and that, most importantly, a recovery of nearly 100% was achieved for the most dilute oocyst concentration (5 oocysts/L).

EXAMPLE 2

To more closely simulate the conditions under which the centrifuge would operate when concentrating naturally occurring Cryptosporidium, live oocysts were spiked into pond water. Recovery efficiencies were compared with those attained using PBS and between two oocyst concentrations in pond water.

Purified live Cryptosporidium oocysts were obtained from Parasitology Research Labs (Phoenix, Ariz.), and diluted with distilled water for a working stock concentration of approximately 15,000 oocysts/mL. Oocysts were spiked by adding the appropriate volume of stock solution to 100 mL of pond water, fixing the Cryptosporidium with formalin (10% final conc.), then mixing the 100 mL aliquot in the larger pond water volume to be centrifuged. These steps were taken to insure that the parasites were killed while minimizing the amount of added formalin.

Cryptosporidium oocysts were spiked into 2, 10, or 15 liters of pond water, collected from the same local pond (Pond 1) on the day of centrifugation. Water was collected from the pond surface with 5 gal buckets where the water depth was at least 50 cm; bottom sediments suspended into the water column by the collector were avoided. The pond water was characterized by two parameters: total solids=49 mg/L and turbidity=2.1 NTU.

Ten liters of water from Pond 1, without added oocysts, were centrifuged as a control. Indigenous Cryptosporidium oocysts were not found. Oocyst target concentrations were 1000 or 100 oocysts/L. The centrifuge feed rate was set at 70 mL/min, and the rotor speed was 2400 rpm (ca. 900×g). Centrifuge times were ½ to 3½ hours. The recovery efficiency was tested 3 times at each oocyst concentration.

The results, presented in FIG. 3, show recoveries of 100% for the most dilute oocyst concentration (100 oocysts/L).

The percentage recoveries were calculated based on the concentration of oocysts retained in the separation channel as compared to the amount of the initial spiking. The supernatants were also examined for oocysts not retained by the centrifuge. Except for the sample feed rates of 250 and 500 mL/min described in Example 3 below, no oocysts were detected in any of the supernatants. Thus it is most likely that parasite separation was close to 100% and the shortfall probably occurs at other steps in the process.

EXAMPLE 3

Recovery of Cryptosporidium Oocysts as a Function of Sample Feed Rate

The time required to concentrate oocysts by continuous centrifugation depends on the sample volume and the sample feed rate into the centrifuge. Given the maximum relative centrifugal force generated by the blood cell separator (900×g), this experiment was conducted to determine the maximum sample feed rate that could be used without reducing recovery efficiency.

Purified live Cryptosporidium oocysts were used as described in Experiment 2. Cryptosporidium oocysts were spiked into 2 or 10 L of water from Pond 1. The target concentration of oocysts was 1000/L for all centrifugation runs. Percent recovery was measured at three sample feed rates: 150, 250, and 500 mL/min. Centrifugation times were 4 minutes to 1 hour.

Samples were pulled into the centrifuge at the desired rate by a peristaltic pump (Cole Parmer, model 7553-20) placed "downstream" from the centrifuge rotor. The built-in centrifuge pumps were bypassed because their maximum pumping rate is only 70 mL/min. Recovery efficiencies were measured 3, 4 or 5 times at each sample feed rate.

Figure 4:
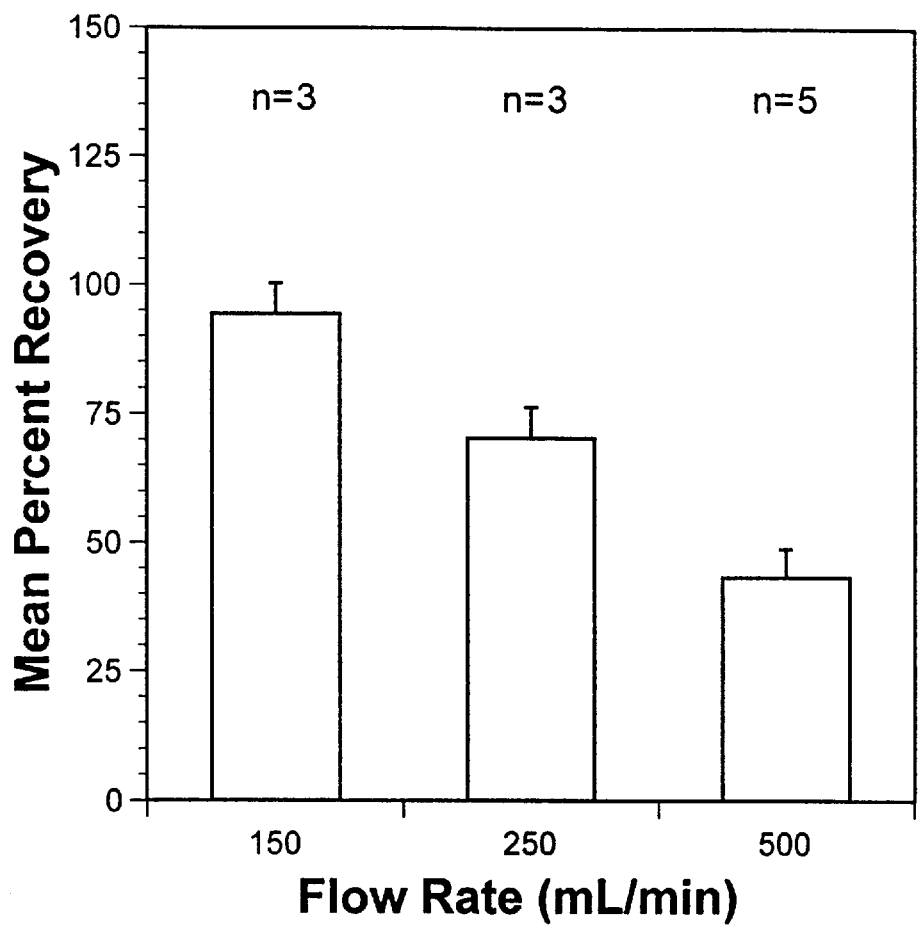

The results, presented in FIG. 4, show recovery rates of between 45–95%, with the highest recovery achieved at the lowest flow rate tested (150 mL/min).

EXAMPLE 4

Recovery of Cryptosporidium From Pond Water, Sample Feed Rate=150 mL/min

Having observed in Example 3 that oocysts could be recovered efficiently when the sample feed rate is 150 mL/min, this example tested whether the recovery efficiency changed with oocyst concentration at that feed rate.

Purified live Cryptosporidium oocysts were used as described in Experiment 2. Cryptosporidium oocysts were spiked into 10 or 25 L of water from another local pond, here denoted Pond 2. For Pond 2, total solids were 182 mg/L, and turbidity was 8.3 NTU.

Ten liters of water from Pond 2 without added oocysts was centrifuged as a control. Indigenous Cryptosporidium oocysts were not found.

Target concentrations were 1000, 100 or 20 oocysts/L. The independent peristaltic pump pulled the samples into the IBM 2997 centrifuge at a flow rate of 150 mL/min. The rotor speed was 2400 rpm (900×g). The time for centrifugation was one to three hours. Recovery efficiencies were measured 3 or 4 times at each Cryptosporidium concentration.

Figure 5:
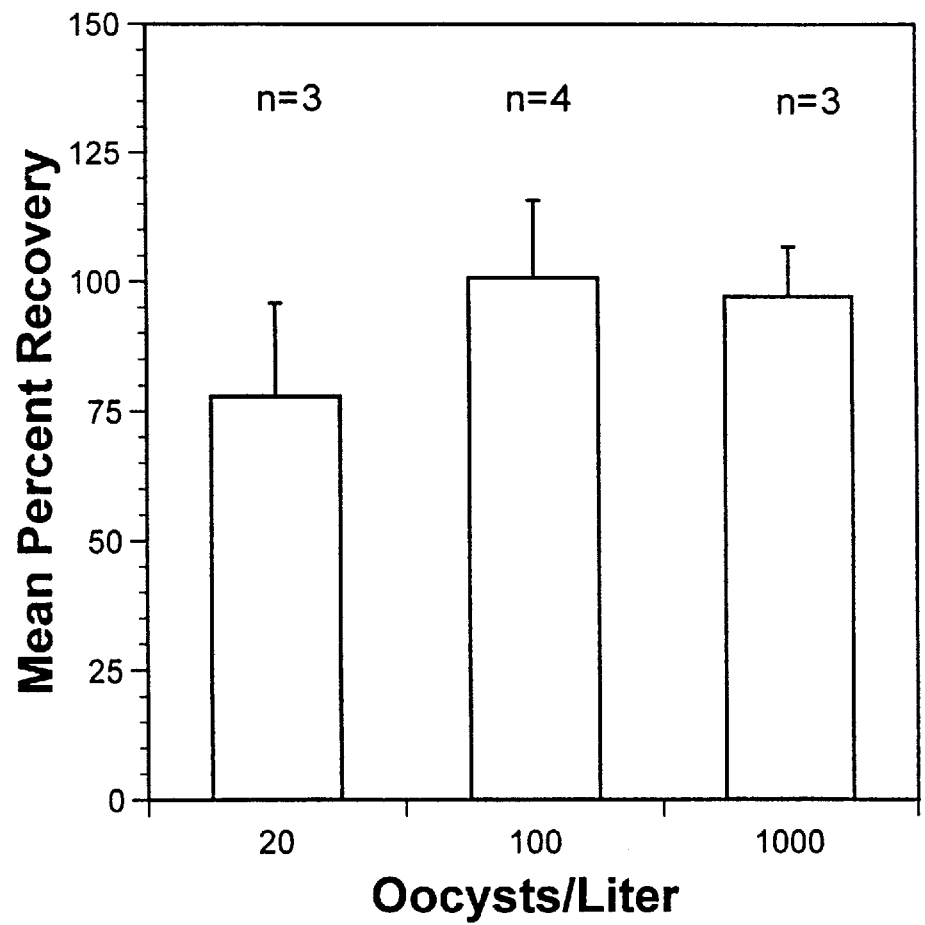

Supernatants were tested as described in Example 1. The results, presented in FIG. 5, show Cryptosporidium recoveries of between 80% and nearly 100%, with the highest recovery achieved at an oocyst concentration of 100 oocyst/L.

EXAMPLE 5

Recovery of *Giardia lamblia* Cysts From Pond Water

The centrifugation process was tested with *Giardia lamblia*, another waterborne protozoan pathogen, to assess whether the centrifuge could efficiently concentrate pathogens larger than Cryptosporidium.

Purified live *Giardia lamblia* cysts were obtained from Parasitology Research Labs (Phoenix, Ariz.) and diluted with distilled water to approximately 22,000 cysts/mL. Cysts were added to water from Pond 2 following the same procedure for Cryptosporidium as described in Experiment 2.

Ten liters of water from Pond 2, without added cysts, were centrifuged as a control. Indigenous Giardia cysts were not found. Giardia cysts were spiked into 10 or 30 L of pond water. Target concentrations of Giardia cysts were 1000, 100 or 20/L. The centrifuge set-up was the same as described in Experiment 4. Sample feed rate was 150 mL/min, and the rotor speed was 2400 rpm. Centrifuge time was 1 to 3½ hours. Recovery efficiencies were measured 3 times at each Giardia concentration.

Figure 6:
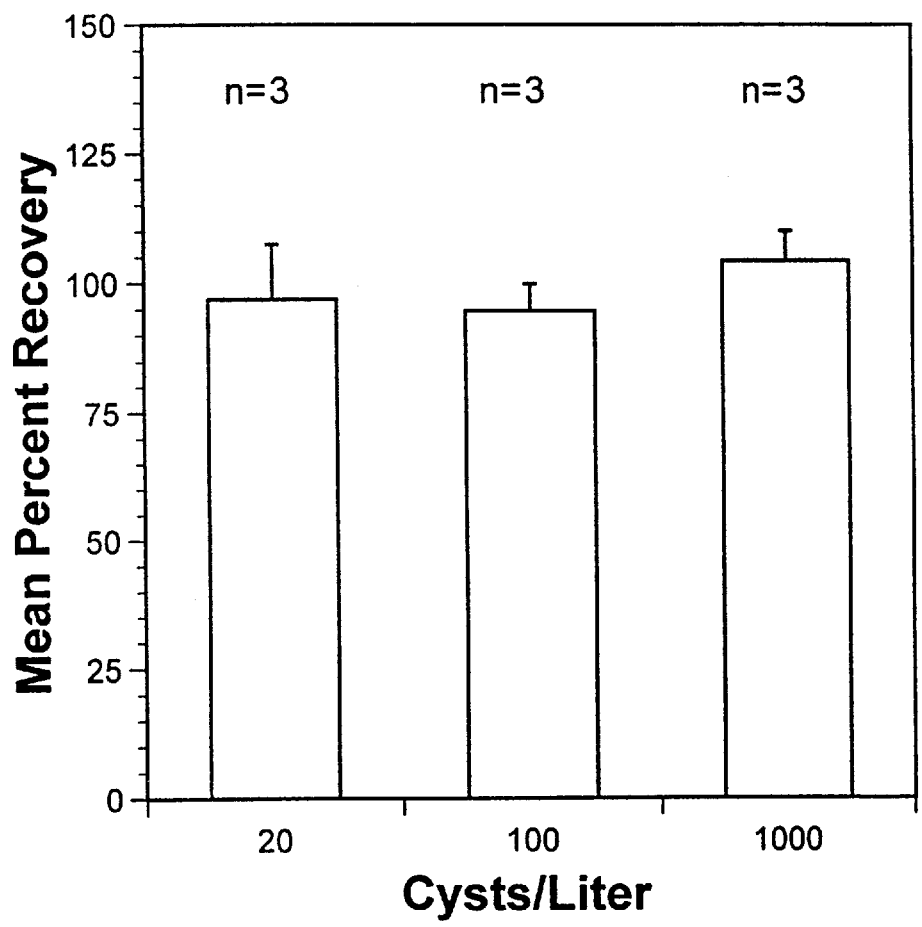

The results, presented in FIG. 6, show recoveries of Giardia cysts to be between 90–100%.

EXAMPLE 6

COBE Spectra centrifuge

The COBE Spectra centrifuge is the latest continuous separation channel centrifuge for blood cell separation. Unlike the IBM 2997 centrifuge, used in the above example, there is no rotating ceramic seal. Instead, the rotation is based on a principle similar to a turning lariat spun by a cowboy. A central vertical core contains the fluid conduits to and from the separation channel which rotates about an axis of rotation extending through that central vertical core. The separation channel itself has a ring shaped geometry similar to the separation channel 12 of FIG. 1.

Purified live Cryptosporidium oocysts were used as described in Experiment 2. Oocysts were spiked into 5 or 7.5 L of water from Pond 2. The oocyst target concentration was 100/L for all centrifuge runs. The input pump of the COBE Spectra centrifuge was set at 150 mL/min, and the rotor speed was 2400 rpm (900×g). The recovery efficiency was tested 3 times.

Using the COBE centrifuge to concentrate Cryptosporidium, 100% of the spiked Cryptosporidium oocysts were recovered.

Compared to the currently approved methods of concentrating *Cryptosporidium* and *Giardia lamblia*, centrifugation with a continuous separation channel centrifuge concentrates and recovers a greater percentage of Cryptosporidium and Giardia oocysts, with less labor and operator attention.

EXAMPLE 7

Recovery of Cryptosporidium Oocysts as a Function of Water Turbidity

An effective method for concentrating parasitic protozoa from water must work over a wide range in water turbidity. In this experiment turbidity was manipulated by concentrating seston in pond water by bulk centrifugation (10,000×g for 15 minutes). For example, to increase turbidity 10-fold above ambient, 10 volumes of pond water were concentrated and the seston pellets added and mixed to the unit volume to be spiked with oocysts. Turbidity was measured using a fluorescence spectrophotometer (Hitachi Model F-4500, excitation and emission wavelengths=500.0 nm, slit width=2.5 nm, and PMT voltage=400 V). Oocysts were spiked into 7.5 L pond water, as described in Example 2, at a target concentration of 100 oocysts/L. Oocysts were recovered with the COBE Spectra centrifuge (rotor speed=2400 rpm, ca. 900×g, sample feed rate=150 mL/min).

Figure 7:
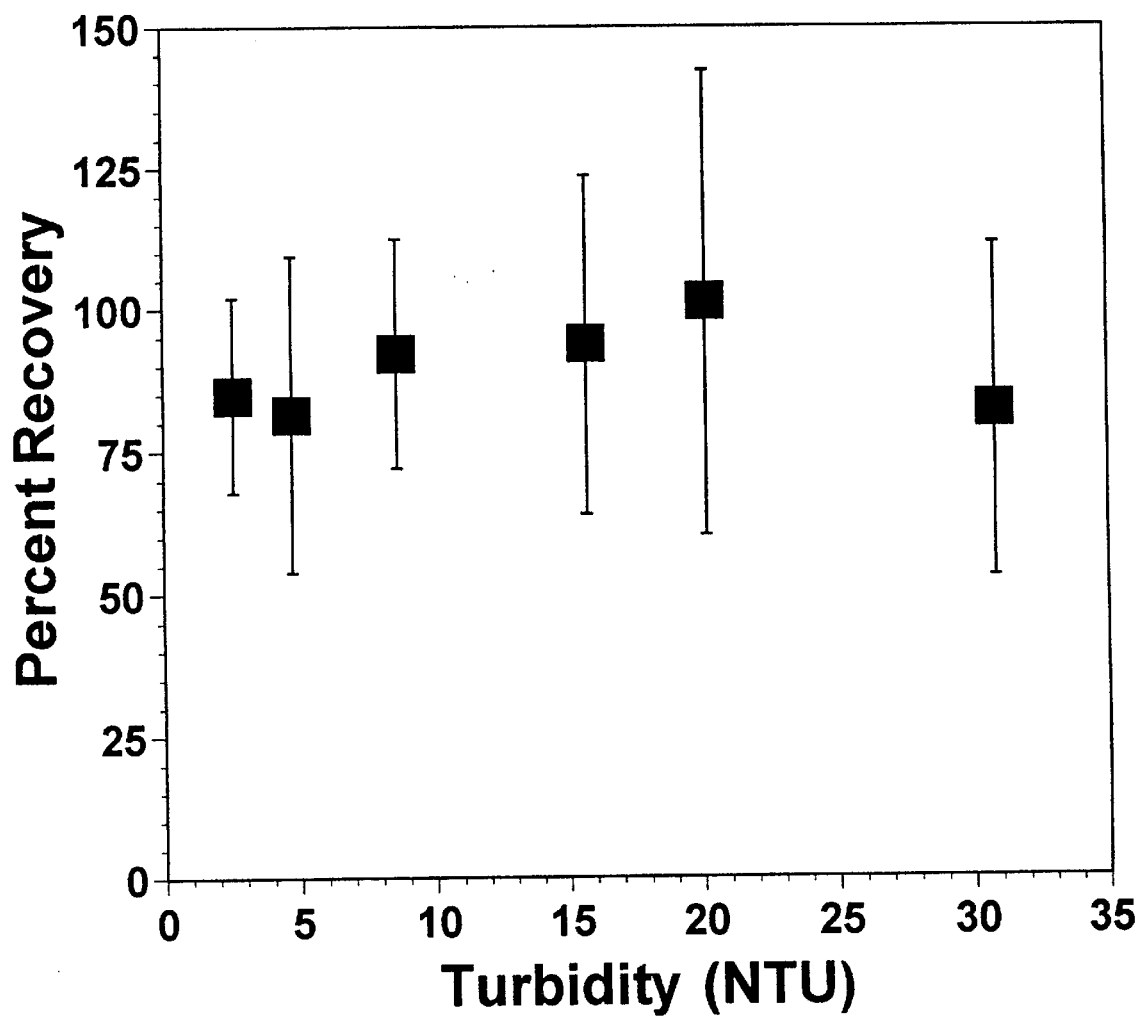

FIG. 7 shows that percent recovery of oocysts did not vary with turbidity levels between 2.6 and 30.8 NTU (F statistic, $p>0.05$, comparison based on count aliquots ($n=6$) because turbidity levels could not be replicated). Error bars represent 1 SD of the mean of 6 counts from the centrifuge concentrate for each turbidity level.

EXAMPLE 8

Recovery of Cryptosporidium from Large Pond Water Volumes

Given that waterborne parasitic protozoa may occur in dilute densities, an effective concentration method must be able to process a large sample volume, on the order of 100 liters. In this experiment live and purified Cryptosporidium oocysts were spiked into 100 L of pond water. Spiking was conducted as described for Example 2. The target density was 100 oocysts/L. Oocysts were recovered with the COBE Spectra centrifuge (rotor speed=2400 rpm, ca. 900×g, sample feed rate=150 mL/min). Centrifugation time for this rotor speed and sample feed rate was 11 hours.

Mean percent recovery of Cryptosporidium oocysts from 100 L of pond water was 94.7±9.7% (mean±1 SD, $n=3$). The recovery efficiency was not significantly different than recovery with the centrifuge and a sample volume of 5 to 7 L (Example 6)(two-tailed t test, $p>0.05$).

The Information Collection Rule, promulgated by the United States Environmental Protection Agency (E.P.A.), requires that all water utilities relying on surface water and serving more than 10,000 residents must routinely monitor for the protozoan parasites *Cryptosporidium* and *Giardia lamblia*. Water could easily be shunted from the intake pipe of a water utility to a continuous centrifuge such as one of the continuous separation channel centrifuges described above. The pre-treated water could be sampled continuously for protozoan parasites, such as *Cryptosporidium* and *Giardia lamblia*, rather than spot-checked as in the presently used methods, which consequently require high sampling labor costs.

It is to be understood that the present invention is not confined to the particular construction and arrangement herein illustrated and described, but embraces such modified forms thereof as come within the scope of the following claims.

What is claimed is:

1. A method of concentrating waterborne protozoan parasites from water potentially contaminated by dilute densities of the parasites, the method comprising the steps of:

a. feeding the water into a separation channel of a continuous separation channel centrifuge; and b. centrifuging the water for a period of time sufficient to collect the protozoan parasites in the channel.

2. The method of claim 1, further comprising the step of coating the separation channel with a surfactant to enhance removal of protozoan parasites from the channel after centrifugation.

3. The method of claim 2, wherein the centrifuge includes a rotating seal assembly and wherein step (a) includes feeding the water through the rotating seal assembly.

4. The method of claim 3, further comprising the step of feeding an aqueous solution of glycerin to the rotating seal assembly to prevent leakage.

5. A method of concentrating *Cryptosporidium oocysts* and *Giardia cysts* from water potentially contaminated by dilute densities of the protozoan parasites, the method comprising the steps of:

a. feeding the water into a separation channel of a continuous separation channel centrifuge; and b. centrifuging the water at a speed such that the relative gravitational force inside the channel is about 900×g, for a period of time sufficient to collect *Cryptosporidium oocysts* and *Giardia cysts* in the channel.

6. The method of claim 5, wherein the water is fed into the separation channel at a flow rate in the range of between about 70 mL/min. and 500 mL/min.

7. The method of claim 6, wherein the flow rate is about 150 mL/min.

8. The method of claim 7, further comprising the step of coating the separation channel with a surfactant to enhance removal of oocysts and cysts from the channel after centrifugation.

9. The method of claim 8, wherein the centrifuge includes a rotating seal assembly and wherein the feeding step includes feeding the water through the rotating seal assembly.

10. The method of claim 9, further comprising the step of feeding an aqueous solution of about 50% glycerin to the rotating seal assembly to prevent leakage.

* * * * *